US011883543B2

(12) United States Patent
Nguyen et al.

(10) Patent No.: US 11,883,543 B2
(45) Date of Patent: Jan. 30, 2024

(54) SYSTEMS AND METHODS FOR PHOTOACTIVATION OF A BIOLOGICAL FLUID

(71) Applicant: Fenwal, Inc., Lake Zurich, IL (US)

(72) Inventors: Lan T. Nguyen, Vernon Hills, IL (US); Angela N. Carlson, Arlington Heights, IL (US); Katherine N. Radwanski, Highland Park, IL (US); Greg Coultas, Chicago, IL (US); Yamen Alshawaf, Burr Ridge, IL (US); Kevin Schalte, Crystal Lake, IL (US)

(73) Assignee: Fenwal, Inc., Lake Zurich, IL (US)

( * ) Notice: Subject to any disclaimer, the term of this patent is extended or adjusted under 35 U.S.C. 154(b) by 666 days.

(21) Appl. No.: 16/834,012

(22) Filed: Mar. 30, 2020

(65) Prior Publication Data

US 2020/0330628 A1 Oct. 22, 2020

Related U.S. Application Data

(60) Provisional application No. 62/834,467, filed on Apr. 16, 2019.

(51) Int. Cl.
*A61L 2/00* (2006.01)
*A61M 1/36* (2006.01)
*A61L 2/24* (2006.01)

(52) U.S. Cl.
CPC ........... *A61L 2/0052* (2013.01); *A61L 2/0047* (2013.01); *A61L 2/24* (2013.01); *A61M 1/3622* (2022.05);

(Continued)

(58) Field of Classification Search
CPC ........ A61L 2/0047; A61L 2/24; A61M 1/3681
See application file for complete search history.

(56) References Cited

U.S. PATENT DOCUMENTS

| 4,321,919 | A | 3/1982 | Edelson |
| 5,360,542 | A | 11/1994 | Williamson, IV et al. |

(Continued)

FOREIGN PATENT DOCUMENTS

WO WO02092138 A1 11/2002

OTHER PUBLICATIONS

European Patent Office, Extended European Search Report, counterpart EP Appl. No. 20168428 (dated Oct. 29, 2020) (7 pages).

*Primary Examiner* — Kevin Joyner
(74) *Attorney, Agent, or Firm* — Cook Alex Ltd.

(57) ABSTRACT

Methods and systems for treating a biological fluid with light are disclosed. The methods and systems provide for determining a target light dose for the biological fluid; loading a treatment container holding the biological fluid into an irradiation chamber of an irradiation device comprising: with the treatment container being supported in the irradiation device in between a first array of light sources and first light energy sensors and a second light energy sensor. The first array of light sources is activated, and a first light intensity is measured with the first light energy sensors. A second light intensity is measured with the second light energy sensor, and the first light intensity is compared to the second light intensity to determine an attenuation factor. The attenuation factor is applied to the first light intensity to determine a time to achieve the target light dose, with the first array of multiple light sources being deactivated after the time to achieve the target light dose has elapsed.

5 Claims, 6 Drawing Sheets

(52) U.S. Cl.
CPC ....... *A61L 2202/14* (2013.01); *A61L 2202/22* (2013.01)

(56) References Cited

U.S. PATENT DOCUMENTS

| | | | |
|---|---|---|---|
| 5,951,509 | A | 9/1999 | Morris |
| 6,027,657 | A | 2/2000 | Min et al. |
| 6,284,142 | B1 | 9/2001 | Muller |
| 7,433,030 | B2 | 10/2008 | Waldo et al. |
| 9,399,093 | B2 | 7/2016 | Min et al. |
| 9,744,288 | B2 | 8/2017 | Min et al. |
| 9,974,899 | B2 | 5/2018 | Radwanski et al. |
| 10,088,492 | B2 | 10/2018 | Wegener et al. |
| 10,172,995 | B2 | 1/2019 | Radwanski et al. |
| 10,213,544 | B2 | 2/2019 | Radwanski |
| 10,363,355 | B2 | 7/2019 | Prendergast et al. |
| 10,434,240 | B2 | 10/2019 | Abedin et al. |
| 10,518,020 | B2 | 12/2019 | Min et al. |
| 10,556,053 | B2 | 2/2020 | Abedin et al. |
| 10,751,433 | B2 | 8/2020 | Crawley et al. |
| 10,886,022 | B2 | 1/2021 | Ali et al. |
| 10,980,933 | B2 | 4/2021 | Prendergast et al. |
| 11,090,397 | B2 | 8/2021 | Min |
| 11,311,823 | B2 | 4/2022 | Kusters et al. |
| 11,318,239 | B2 | 5/2022 | Ali et al. |
| 2016/0114095 | A1 | 4/2016 | Radwanski |
| 2016/0195555 | A1* | 7/2016 | Wegener ................ G01N 33/80 435/39 |
| 2017/0028121 | A1 | 2/2017 | Manzella et al. |
| 2017/0029776 | A1 | 2/2017 | Cork et al. |
| 2017/0197023 | A1 | 7/2017 | Radwanski et al. |
| 2018/0078694 | A1 | 3/2018 | Abedin et al. |
| 2018/0147306 | A1 | 5/2018 | Crawley et al. |
| 2019/0099544 | A1 | 4/2019 | Abedin |
| 2019/0224494 | A1 | 7/2019 | Radwanski et al. |
| 2020/0107765 | A1 | 4/2020 | Abedin et al. |
| 2020/0188685 | A1 | 6/2020 | Coultas et al. |
| 2020/0222620 | A1 | 7/2020 | Ali et al. |
| 2020/0297914 | A1 | 9/2020 | Radwanski et al. |
| 2021/0038802 | A1 | 2/2021 | Madsen |
| 2021/0052804 | A1 | 2/2021 | Madsen |
| 2021/0154390 | A1 | 5/2021 | Radwanski et al. |

* cited by examiner

SYSTEMS AND METHODS FOR PHOTOACTIVATION OF A BIOLOGICAL FLUID

FIELD OF THE DISCLOSURE

The present disclosure is directed to systems and methods for treating a biological fluid with light. More particularly, the present disclosure is directed to systems and methods for treating a biological fluid with light where an initial target time of exposure is determined based on the amount of light that passes through the treatment container and the time of exposure is dynamically controlled to account for variations in light intensity over the course of the treatment.

BACKGROUND

An irradiation device is particularly useful in certain treatments of biological fluids. As used herein, biological fluid refers to any fluid that is found in or that may be introduced into the body including, but not limited to, blood and blood products. As used herein, "blood product" refers to whole blood or a component of whole blood such as red blood cells, white blood cells, platelets, plasma or a combination of one or more of such components that have been separated from whole blood.

For example, an irradiation device may be used in the treatment of a blood product that has been combined with a photochemical agent for activation when subjected to light. Such photochemical agents are used, for example, in the inactivation of viruses, bacteria, and other contaminants (collectively referred to herein as "pathogens"). Photochemical agents are also used in the treatment of mononuclear cells, such as white blood cells. In the treatment of mononuclear cells, the activated agent targets the mononuclear cell itself as part of a treatment of a disease or a side effect of a mononuclear cell therapy. One such treatment of mononuclear cells (MNCs) is referred to as extracorporeal photopheresis.

In an extracorporeal photopheresis (ECP) procedure, collected MNCs are treated with a combination of UV-A light and 8-Methoxypsoralen (8-MOP). If delivered in the right dosage, this combination causes an apoptotic response in the treated MNCs. This response is the desired treatment for conditions such as cutaneous T-Cell lymphoma (CTCL), acute and chronic graft versus host disease (GvHD), and heart and lung transplant rejection.

During an extracorporeal photopheresis procedure, an MNC collection is carried out to collect MNCs to be treated. Then, 8-MOP is injected or otherwise delivered into the treatment container (which may be the MNC collection container used during MNC collection procedures) and this mixture is photoactivated in an irradiation device with UV-A light. The treated cells are then re-infused into the patient. Systems and methods for performing ECP are described in U.S. Patent Application Publication US2014/0370491 and U.S. Pat. No. 9,399,093, both of which are incorporated by reference herein in their entireties. Examples of irradiation devices useful in carrying out ECP procedures are described in U.S. Patent Application Publications US 2017/0028121, US 2017/0029776 and US 2018/0147306, all of which are also incorporated by reference herein in their entireties.

The irradiation device typically includes one or more light sources and a UV sensor(s) that measure the amount of light being delivered by the UV-A light sources and a controller that controls how long the UV-A light sources remain activated based on the intensity of UV-A light sensed. An algorithm integrates the UV-A light intensity over time to arrive at a total UV-A light dose emitted value (e.g., target dose). However, the algorithm does not account for the presence in the biological fluid to be treated of cellular material that blocks the light from reaching the targeted cells. Most commonly, such light-attenuating cellular material comprises red blood cells, with the volume percent of red blood cells in the suspension to be treated being the hematocrit of the suspension. As a result, the algorithm tends to deliver a light dose on the lower end of the targeted range for high-hematocrit products and on the higher end of the targeted range for low-hematocrit products.

In addition, the intensity of the UV-A light sources can vary over the course of the treatment time, which results in further difficulties in controlling the light dose delivered to the targeted cells.

Therefore, there is a need to develop a method for photoactivation that can account for both the amount of light attenuating material present with the targeted cells and for variations in the light intensity over the course of treatment so that the targeted light dose is delivered.

SUMMARY

In a first aspect, the present disclosure is directed to an irradiation device for treating a biological fluid with light. The device includes a housing defining an irradiation chamber, with a tray located interior of the irradiation chamber for supporting a container of the biological fluid to be treated. A first array of multiple light sources is mounted in the housing on a first side of the tray, with a first light energy sensor is associated with each light source of the first array, so that the first array and first light energy sensors are disposed in the irradiation device on a first side of the irradiation chamber. A second light energy sensor is mounted in the housing on the second side of the tray, such that a treatment container can be supported in the irradiation device in between the first array of multiple light sources and first light energy sensors and the second light energy sensor. A programmable controller associated with the irradiation device that includes an operator input for receiving a target light dose and is configured to automatically operate the irradiation device in accordance with the method of the second aspect described below. Preferably, the irradiation device includes a second array of multiple light sources mounted in the housing on the second side of the tray, with a light sensor associated with each of the multiple light sources in the second array.

In a second aspect, the present disclosure is directed to a method for treating a biological fluid with light using an irradiation device as described above. First, a target light dose for the biological fluid is determined, which is input into the programmable controller. After loading a treatment container holding the biological fluid into the irradiation chamber of an irradiation, the first array of multiple light sources are activated; a first light intensity is measured with the first light energy sensors; a second light intensity is measured with the second light energy sensor; and the first light intensity is compared to the second light intensity to determine an attenuation factor. The attenuation factor is applied to the first light intensity to determine a time to achieve the target light dose. After the time to achieve the target light dose has elapsed, the first array of multiple light sources is deactivated. Preferably, the first light intensity is continuously measured with the attenuation factor applied and integrated over time to account for variations in the first light intensity over time, with the time to achieve the target dose being adjusted accordingly. Further, the first light intensity may be determined by summing a light energy measured by each of the first photodiodes.

DETAILED DESCRIPTION OF THE EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
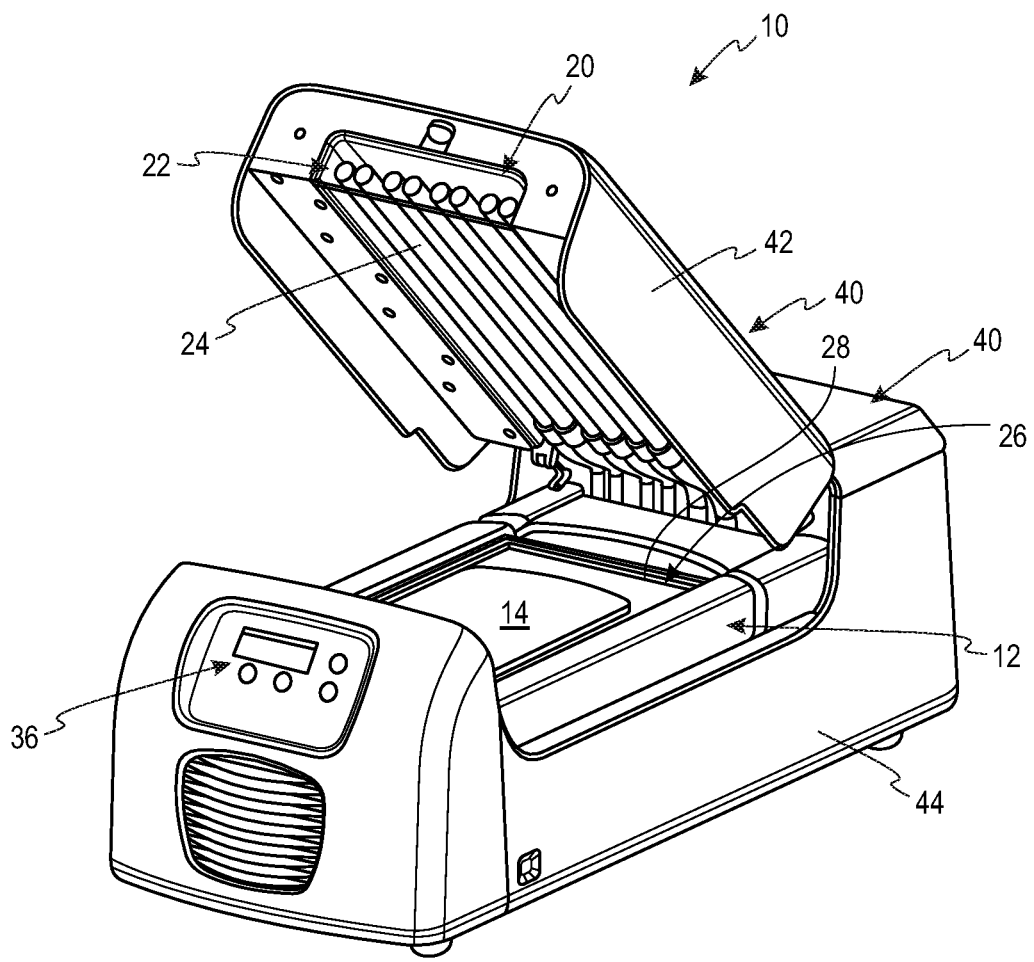
FIG. 1 is a perspective view of an embodiment of a device used to irradiate a biological fluid in a biological fluid container.
Figure 2:
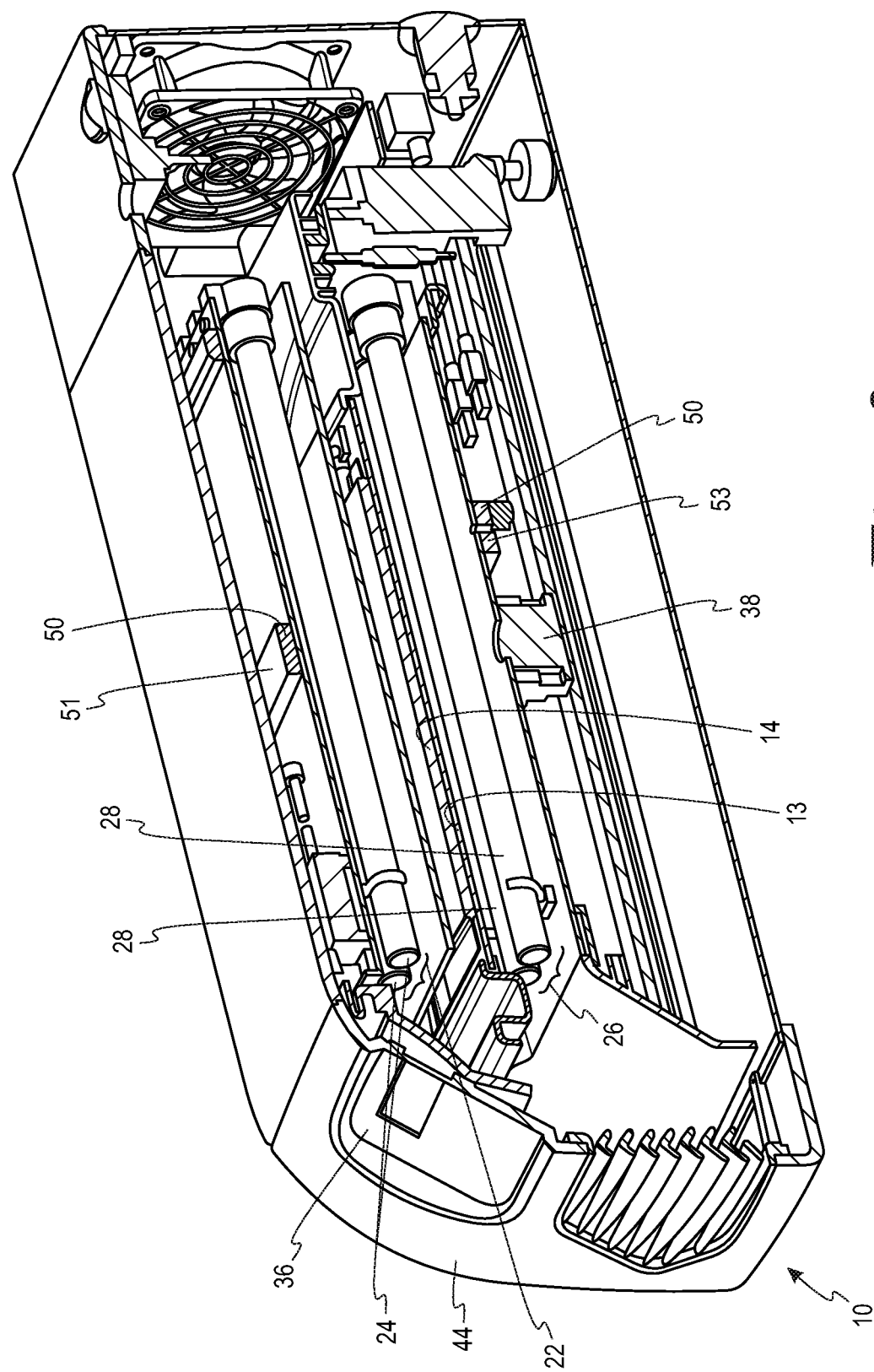
FIG. 2 is a perspective view, in cross section, of the irradiation device of FIG. 1.

As illustrated in FIG. 1, an irradiation device 10 includes a fluid treatment/irradiation chamber 12 having a tray 13 configured to support a container 14 of the biological fluid to be treated. As illustrated in FIGS. 1 and 2, device 10 also includes at least one light source 20 disposed adjacent at least one of the first and second sides of the tray 13 of fluid treatment/irradiation chamber 12. Light source 20 may include, for example, a first upper array 22 with a plurality of light sources 24 disposed on first side of the tray 13 and a second lower array 26 with a plurality of light sources 28 disposed on second side of the tray 13.

According to an embodiment of the present disclosure, light sources 24, 28 are similar in structure and operation, and provide electromagnetic radiation in the ultraviolet portion of the spectrum (e.g., UVA). An alternative device is described in U.S. Pat. No. 7,433,030, the contents of which are incorporated by reference herein in its entirety. Device 10 may include an agitator, as shown and described in U.S. Patent Application Publication US 2017/0029776, previously incorporated by reference, coupled to fluid treatment chamber 12 to move at least a part of fluid treatment chamber 12 with an oscillatory motion. Agitator may include a motor in combination with a linkage (such as a rotating cam), the linkage coupling the motor to fluid treatment chamber 12.

As further shown in FIG. 1, device 10 may also include a housing 40 in which fluid treatment chamber 12 is defined, and in which light source 20, agitator, and other components of device 10, including one or more sensors 38 and controller 39 (described in greater detail below) are disposed. While FIG. 1 illustrates an embodiment of housing 40 including a lid 42 that may be moved pivotally relative to a base 44 to open housing 40 and permit access to fluid treatment chamber 12, it will be recognized that according to other embodiments of device 10, housing 40 may instead include a sliding drawer that permits access to fluid treatment chamber 12.

One or more sensors (e.g., one or more of a UV sensor, a volume or weight detector or scale, a viscosity detector, a temperature sensor, an air detector, and a density detector) are disposed within the fluid treatment chamber for measuring a condition of the biological fluid in the fluid container 14. Preferably, the sensors are mounted within or near the fluid treatment chamber in proximity to the fluid being treated. According to different embodiments, a single sensor may be provided, or a plurality of sensors may be provided to measure the various sensed conditions.

In one embodiment, one or more light energy sensors (e.g., PMA1110-F from Solar Light Technologies) is/are disposed within or near the fluid treatment chamber for measuring the intensity of the light being delivered and ultimately the amount of light energy (dose) to which the fluid container 14 is subjected. Preferably, the light energy sensors are mounted within the fluid treatment chamber in relative proximity to the fluid container so as to more accurately determine the light energy reaching the fluid container 14 and, thus, whether or not the biological fluid has been sufficiently treated.

Figure 3:
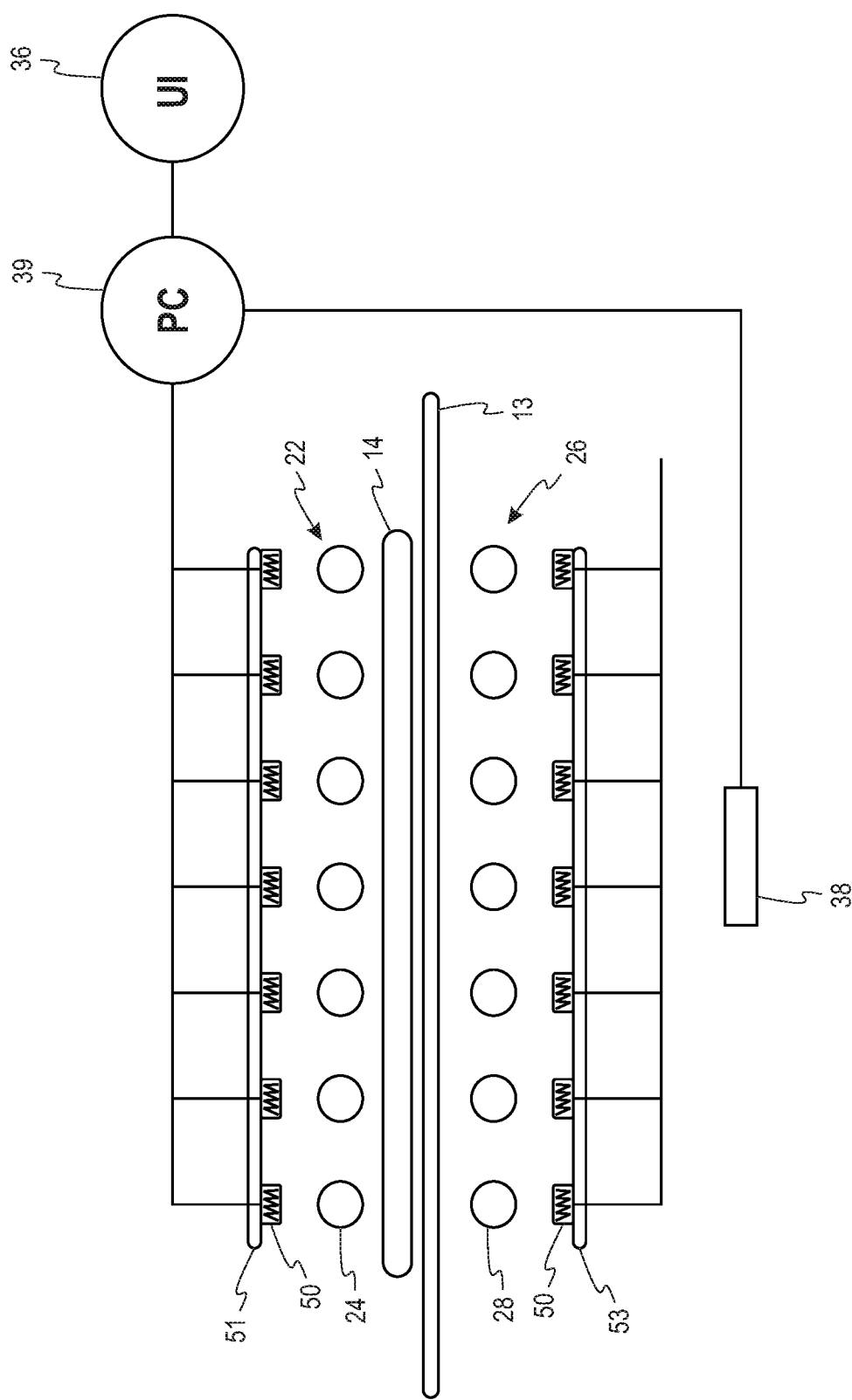
FIG. 3 is a block diagram of an embodiment of the electronic components of the irradiation device of FIG. 1 or ECP system generally.

According to the illustrated embodiment, a single "main" sensor 38 may be provided (seen in FIG. 2), and/or a plurality of additional sensors may be provided. In accordance with the present disclosure, in addition to a single main light energy sensor 38, each of the individual light sources 24, 28 (bulbs) of arrays 22 and 26 may be coupled to a sensor 50. As shown in FIG. 2, a board 51 carrying a sensor 50 for each individual bulb is centered over each bulb 24 of array 22. Similarly, board 53 carries sensors centered over each bulb 28 of array 26. FIG. 3 schematically shows each light source 24, 28 within each array 22, 26 coupled it its own sensor 50 that monitors the output of the particular light source 24, 28. As further seen in FIG. 3, each sensor 50 is likewise coupled to controller 39. Thus, as shown in FIG. 3, main light sensor 38 and/or individual light sensors 50 may be coupled to controller 39.

Controller 39 may take the form of one or more electrical components or circuits, and comprises a processor and an associated memory according to one embodiment. According to such an embodiment, the processor may be programmed to carry out any of the actions that controller 39 is described as being configured to perform below. The instructions by which the processor is programmed may be stored on the memory associated with the processor, which memory may include one or more tangible non-transitory computer readable memories, having computer executable instructions stored thereon, which when executed by the processor, may cause the one or more processors to carry out one or more actions.

A detailed description of an entire ECP procedure is beyond the scope of the present disclosure and, in any event, can be gleaned from U.S. Patent Application Publication US2014/0370491 and U.S. Pat. No. 9,399,093, both of which are incorporated by reference. However, a general overview of the ECP system is provided below.

Figure 4:
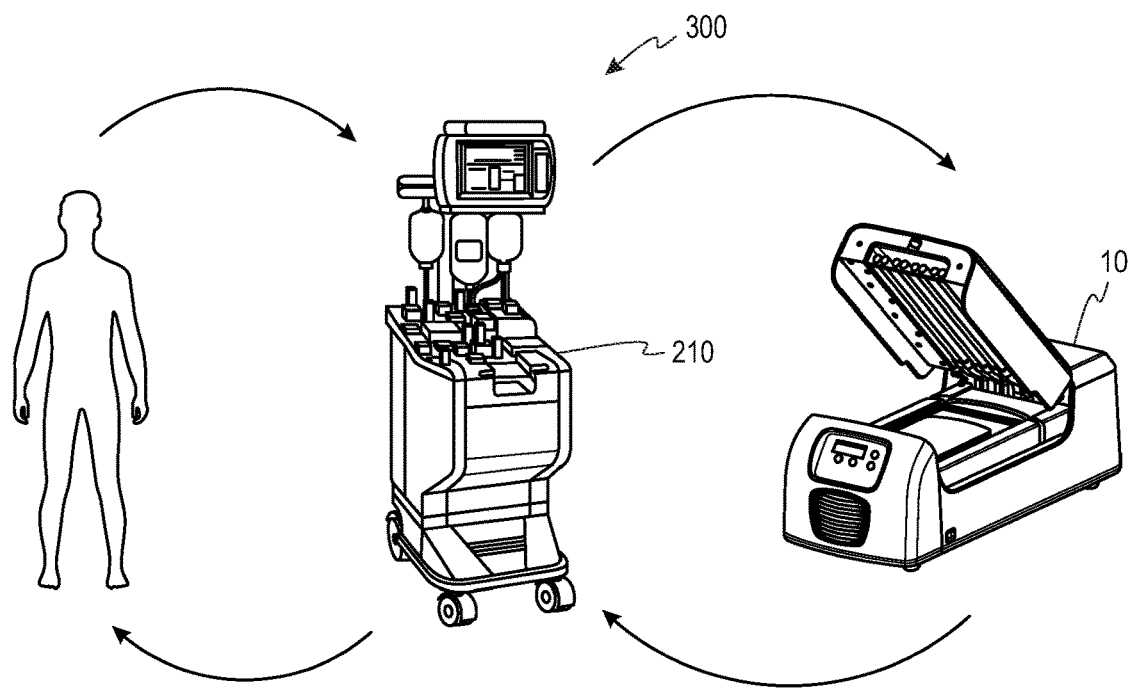
FIG. 4 is a diagram of an embodiment of a system including the irradiation device of FIG. 1 in combination with a cell separator.
Figure 5:
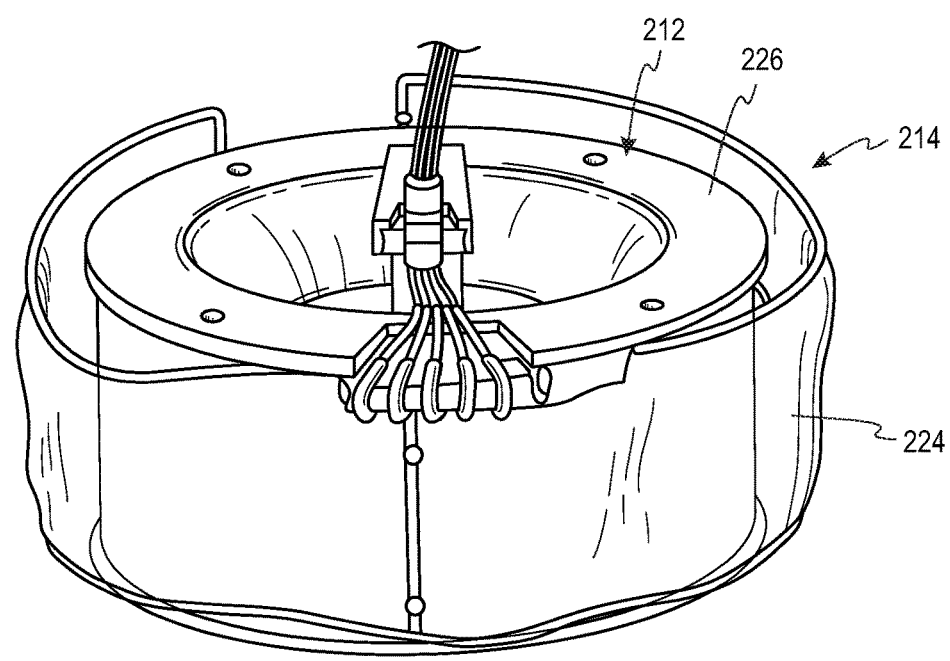
FIG. 5 is a perspective view of a processing container (separation chamber) of a processing set used with the separator of FIG. 4.
Figure 6:
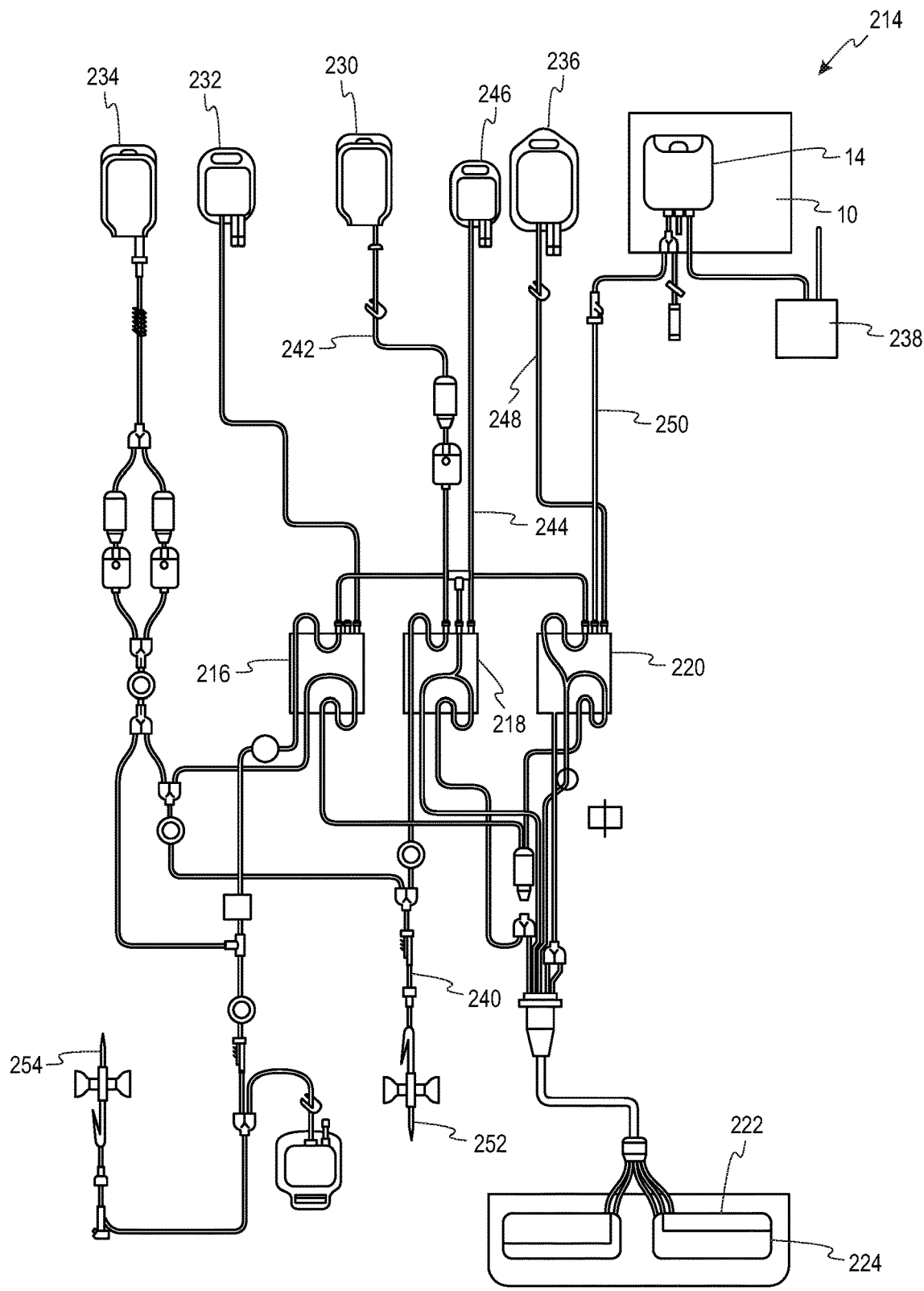
FIG. 6 is a diagram of a processing set for used with the separator of FIG. 4.

The irradiation device 10 may be used as a stand-alone device, or it may also be used in conjunction with a cell separator 210 as part of a system 300, as illustrated in FIGS. 4-6. With reference to FIGS. 4-6, system 300 includes a cell separator 210 and irradiation device 10. Cell separator 210 would be configured to direct a biological fluid into a biological fluid container (e.g., container 14), and irradiation device 10 would include fluid treatment/irradiation chamber 12 configured to receive biological fluid container 14. The cell separator 210 may be an Amicus® Separator made and sold by Fenwal, Inc., of Lake Zurich, Illinois, a subsidiary of Fresenius-Kabi of Bad Homburg, Germany. Mononuclear cell collections performed using a device such as the Amicus® are described in greater detail in U.S. Pat. No. 6,027,657, the contents of which is incorporated by reference herein in its entirety.

Briefly, FIGS. 4-6 show separator 210 in FIG. 4, a representative blood centrifuge 212 (defining part of the separator 210) with a portion of a fluid circuit 214 mounted thereon in FIG. 5, and the entire fluid circuit 214 in FIG. 6. Fluid circuit (also referred to as a processing set) 214 includes a plurality of processing fluid flow cassettes 216, 218 and 220 (see FIG. 6) with tubing loops for association with peristaltic pumps on device 210. Fluid circuit 214 also includes a network of tubing and pre-connected containers for establishing flow communication with the patient and for processing and collecting fluids and blood and blood components, as shown in greater detail in FIG. 6.

As illustrated in FIGS. 5 and 6, a separation chamber 222 is defined by the walls of a flexible processing container 224 carried within an annular gap defined by a rotating spool element 226 (see FIG. 5) and an outer bowl element (not shown). The processing container 224 takes the form of an elongated tube that is wrapped about the spool element 226 before use. The bowl and spool element 226 are pivoted on a yoke between an upright position and a suspended position, also not shown. In operation, the centrifuge 212 rotates the suspended bowl and spool element 226 about an axis, creating a centrifugal field within the processing chamber of container 224. Details of the mechanism for causing relative movement of the spool 226 and bowl elements as just described are disclosed in U.S. Pat. No. 5,360,542, the contents of which is also incorporated by reference herein in its entirety.

As seen in FIG. 6, the disposable processing set 214 may include the flexible processing container 14, as well as a container 230 for supplying anticoagulant, a waste container 232 for collecting waste from one or more steps in the process for treating and washing mononuclear cells, a container 234 for holding saline or other wash or resuspension medium, a container 236 for collecting plasma, container 14 for collecting mononuclear cells from the operation discussed relative to FIG. 5 and, optionally, a container 238 for holding a photoactivation agent or other device (such as a syringe for delivering the agent.

Container 14 is preferably pre-attached to with the disposable set 214. Alternatively, container 14 may be attached to set 214 by known sterile connection techniques, such as sterile docking or the like. With reference to FIG. 6, fluid circuit includes inlet line 240, an anticoagulant (AC) line 242 for delivering AC from container 230, an RBC line 244 for conveying red blood cells from chamber 222 of container 224 to container 246, a platelet-poor plasma (PPP) line 248 for conveying PPP to container 236 and line 250 for conveying mononuclear cells to and from separation chamber 222 and collection/illumination container 14. The blood processing set 214 includes one or more venipuncture needle (s) for accessing the circulatory system of the patient. As shown in FIG. 6, fluid circuit 214 includes inlet needle 254 and return needle 252. In an alternative embodiment, a single needle can serve as both the inlet and outlet needle.

Container 14 is suitable for irradiation by light of a selected wavelength. By "suitable for irradiation", it is meant that the walls of the container are sufficiently translucent to light of the selected wavelength. In treatments using UVA light, for example, container walls made of ethylene vinyl acetate (EVA) are suitable. Accordingly, container 14 in which the mononuclear cells are collected may serve both as the collection container and the irradiation container. Container 14 may be placed inside irradiation device 10 by the operator or, more preferably, may be placed inside the irradiation chamber of irradiation device 10 at the beginning of a procedure including the cell separator and prior to whole blood withdrawal (as shown by the broken lines representing device 10 in FIG. 6). Preferably container 14 remains integrally connected to the remainder of fluid circuit 214 during the entire procedure, thereby maintaining the closed or functionally closed condition of fluid circuit 214.

Fluid flow through fluid circuit 214 is preferably driven, controlled and adjusted by a microprocessor-based controller in cooperation with the valves, pumps, weight scales and sensors of device 210 and fluid circuit 214, the details of which are described in the previously mentioned U.S. Pat. No. 6,027,657. In this regard, automated control of the MNC collection and the irradiation treatment may be effected by the microprocessor-based controller of the respective separation device 210 and irradiation device 10 with some operator input for each device. Alternatively, operation of both separation device 210 and irradiation device 10 and the process steps carried out by each may be remotely controlled by a separate controller (e.g., a computer) that communicates with both.

The total amount of light energy to which the biological fluid in the container is to be subjected during the irradiation cycle may be either preprogrammed into the controller 39 or input by the operator through the user interface 36. In accordance with the present disclosure, the controller will then determine an attenuation factor based on the amount of light transmitted through the treatment container from one of the light arrays, then determine a duration of the treatment based on the attenuation factor and the output of the light sources 24, 28 within both arrays 22, 26, the sensors associated with each of the arrays measuring the UV-A output.

In order to determine the duration of treatment, two sets of values are preferably programmed into the controller. The first set of values is the result of experimental data where treatment containers with known hematocrit are loaded, and the first attenuation factor measured. Then, during a procedure, the measured first attenuation factor can be interpolated with these known values to determine an approximate hematocrit value for the product.

The second set of values is the result of experimental data where treatment containers with known hematocrit are dosed with a known amount of UV-A output (J) from the bulbs, and the actual amount of dose received by the cells is measured and used to determine a second attenuation factor (ratio of the UVA dose received by cells vs. UVA dose emitted). With the approximate hematocrit as determined above, the second corresponding attenuation factor, and the knowledge of the desired dose to be received by the cells, the necessary amount of UV-A output can then be interpolated. The irradiation cycle may then be initiated, with the light sources 24, 28 being activated, thereby illuminating biological fluid container 14 in fluid treatment/irradiation chamber 12. The amount of UV-A intensity (mW) will be directly measured by the sensor arrays, and these measurements will be integrated until the desired output has been achieved. The integration of UV-A intensity until the target output is reached allows for handling of the fluctuation in bulb output over the treatment. The fluid container 14 is preferably oscillated by activating the agitator at the initial rate; thereby agitating biological fluid container 14 while biological fluid container 14 is illuminated.

Methods for a photoactivation procedure in accordance with the present disclosure will now be described. Once the container of biological fluid that is to be treated is loaded into the irradiation device, one array of bulbs is turned on and measurements of the UVA intensity at all photodiodes would be taken. UVA light is transmitted directly to the photodiodes closest to the bulbs (e.g. the upper photodiodes, if the upper array of bulbs is turned on), whereas the UVA light will be transmitted through the container of biological fluid to reach the other photodiodes (e.g. the lower photodiodes, if the top array of bulbs is turned on). Alternatively, a different sensor, such as the UVA sensor 38, or another photodiode, could be used to take this measurement from one of the bulb arrays through the treatment container. The ratio of the readings from the photodiodes receiving direct light compared to those receiving light transmitted through the object correlates to the attenuation factor relating to the amount of light attenuating matter in the container.

Once photoactivation is started, the controller continues to take readings from each bulb sensor. Using the known contribution from each bulb to UVA intensity at the treatment container, the individual sensor readings are summed to determine the overall UVA intensity at the treatment container, to which the correction factor is applied to arrive at a time of treatment required to deliver the targeted total light energy to be delivered to the treatment container. The corrected overall UVA intensity is integrated over the course of the photoactivation until the target dose is achieved to result in expected photoactivation times that are dependent on both the intensity of light emitted by the bulbs and the amount of light attenuating matter in the treatment container.

Figure 7:
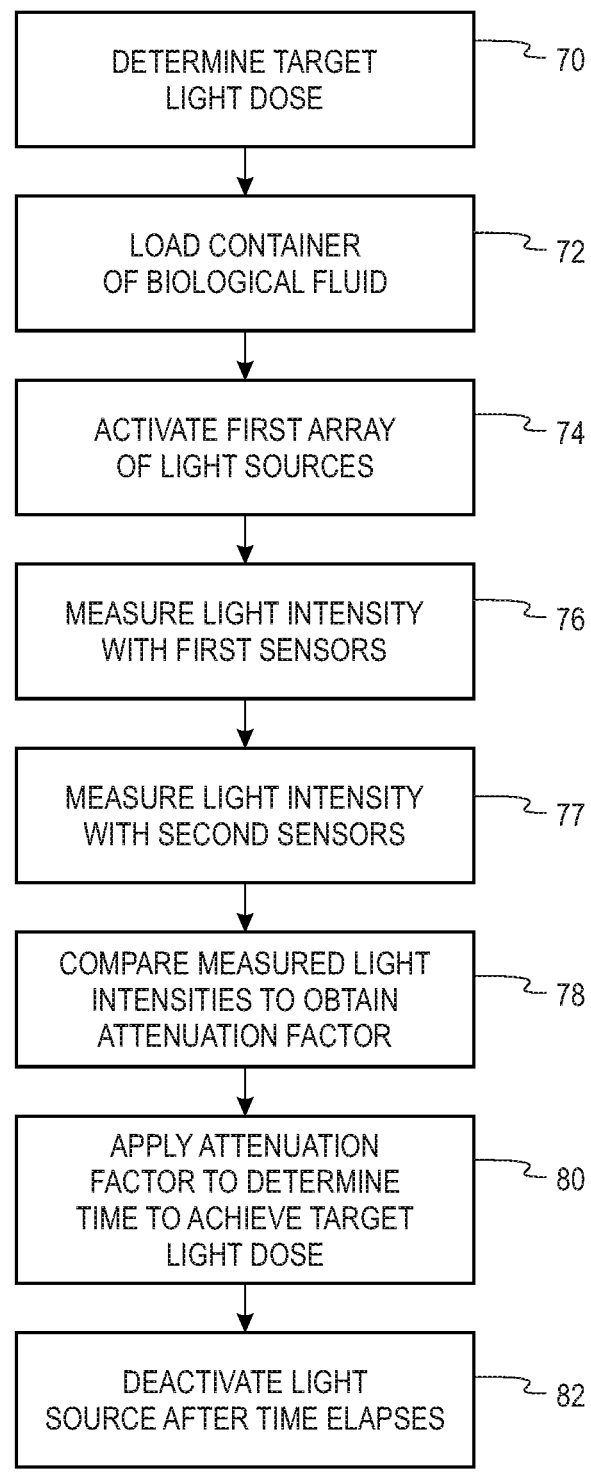
FIG. 7 is a flow diagram depicting a method of photoactivation of a biological fluid in accordance with the present disclosure.

Thus, as shown in FIG. 7, the first steps include determining the target light dose for the biological fluid in the treatment container (step 70) and loading the container of biological fluid into the treatment chamber of the irradiation device (step 72). Steps 70 and 72 may be performed in either order. The target light dose may be input into the programmable controller by the operator, or it may be pre-programmed into the controller for the particular biological fluid being treated.

The first array of light sources are then activated (step 74). A first measurement of the light intensity is taken with the sensors adjacent the first array of light sources (step 76) and a second measurement of the light intensity is taken with the sensor or sensors located on the opposite side of the tray from the first array of light sources so that the second sensor/sensors measure light intensity after the light has passed through the treatment container.

The two light intensity measurements are then compared (step 78). The ratio of the light intensity measured by the second sensor/sensors to the light intensity measured by the first sensors corresponds to the amount of light energy blocked by attenuating matter (such as red blood cells) in the treatment container, and provides the attenuation correction factor. The attenuation factor is applied to the light intensity provided by the first array of light sources to determine the time to achieve the target light dose (step 80). If the irradiation device has a second array of light sources (as does the irradiation device described above), the attenuation factor is also applied to the light intensity provided by the second array as measured by the second sensors. The corrected values for the light intensity provided by the first and second arrays of light sources is then summed to arrive at the total light energy delivered, and this value is used to determine the time to achieve the target light dose.

The activated light sources are then operated until the time to achieve the target light dose has elapsed, after which the light sources are deactivated (step 82). The programmable controller preferably operates the irradiation device to automatically perform steps 74-82 described above.

The intensity of light emitted by light sources may vary over the time of treatment. To account for any such variations, the controller preferably continuously monitors the light intensities provided by the light sources over the course of treatment, with the attenuation factor being applied, integrates the values to determine the total amount of light energy that has been delivered, and, if necessary adjusts the time to achieve the target dose based on the current light intensity measurement.

Several advantages accrue to this protocol. First, accounting for the amount of light attenuating matter in the treatment container allows for adjustment of the treatment time to better target the center of the targeted dose range for biological fluids that have extreme amounts (low or high) of light attenuating matter. Also, this method is more effective under various failure modes. In predicate ECP systems that use intensity and a hematocrit sensor to determine the photoactivation time, a failure of the hematocrit sensor could result in excessive photoactivation times up to 90 minutes. A single point failure in this setup would not result in an excessive photoactivation time. Also, by using the multi-sensor array, with a sensor associated with each light source, individual bulb failures are accounted for in the algorithm used since the decreased calculated intensity would result in a longer photoactivation time. Individual sensor failures or individual bulb failures may also be addressed by removing power to the part of the array that has either a sensor or a bulb failure, and then integrating the remaining active bulb output.

Without limiting any of the foregoing, the disclosed device, method and system may include one or more of the aspects set forth below.

OTHER EXAMPLES

Aspects of the present subject matter described above may be beneficial alone or in combination with one or more other aspects, as described below.

In a first aspect, a method for treating a biological fluid with light is provided comprising: determining a target light dose for the biological fluid; loading a treatment container holding the biological fluid into an irradiation chamber of an irradiation device comprising: i) a first array of multiple light sources, ii) a first light energy sensor associated with each light source of the first array, the first array and first light energy sensors being disposed in the irradiation device on a first side of the irradiation chamber, and iii) a second light energy sensor disposed on a second side of the irradiation chamber, such that the treatment container is supported in the irradiation device in between the first array of multiple light sources and first light energy sensors and the second light energy sensor; activating the first array of multiple light sources, measuring a first light intensity with the first light energy sensors; measuring a second light intensity with the second light energy sensor; comparing the first light intensity to the second light intensity to determine an attenuation factor; applying the attenuation factor to the first light intensity to determine a time to achieve the target light dose; and deactivating the first array of multiple light sources after the time to achieve the target light dose has elapsed.

In a second aspect, the method further comprises continuously measuring the first light intensity and applying the attenuation factor and integrating over time to account for variations in the first light intensity over time and adjusting the time to achieve the target dose accordingly.

In a third aspect, the first light energy sensors comprise photodiodes and the second light energy sensors comprise one of a UV-A sensor and one or more second photodiodes.

In a fourth aspect, the first light intensity is determined by summing a light energy measured by each of the first photodiodes.

In a fifth aspect, a device for treating a biological fluid with light is provided comprising: a housing defining an irradiation chamber; a tray having a first side and a second side located interior of the irradiation chamber for supporting on the first side a container of the biological fluid; a first array of multiple light sources mounted in the housing on the first side of the tray; a first light energy sensor mounted in the housing on the first side of the tray in association with each of the multiple light sources in the first array; a second light energy sensor mounted in the housing on the second side of the tray; and a programmable controller having an operator input for receiving a target light dose for the biological fluid and configured to automatically: i) activate the first array of multiple light sources, ii) measure a first light intensity with the first light energy sensors, iii) measure a second light intensity with the second light energy sensor, iv) comparing the first light intensity to the second light intensity to determine an attenuation factor, v) apply the attenuation factor to the first light intensity to determine a time to achieve the target light dose, and vi) deactivate the first array of multiple light sources after the time to achieve the target light dose has elapsed.

In a sixth aspect; the programmable controller is further configured to continuously measure the first light intensity, apply the attenuation factor and integrate over time to account for variations in the first light intensity, and adjust the time to achieve the target light dose accordingly.

In a seventh aspect, the first light energy sensors comprise photodiodes.

In an eighth aspect, the second light energy sensor comprises a UV-A sensor.

In a ninth aspect, the device further comprises a second array of multiple light sources mounted in the housing on the second side of the tray and wherein the second light energy sensor comprises a photodiode associated with each of the multiple light sources in the second array.

The invention claimed is:

1. A device for treating a biological fluid with light comprising:
   a) a housing defining an irradiation chamber;
   b) a tray having a first side and a second side located interior of the irradiation chamber for supporting on the first side a container of the biological fluid;
   c) a first array of multiple light sources mounted in the housing on the first side of the tray;
   d) first light energy sensors mounted in the housing on the first side of the tray in association with each of the multiple light sources in the first array;
   e) a second light energy sensor mounted in the housing on the second side of the tray; and
   f) a programmable controller having an operator input for receiving a target light dose for the biological fluid and configured to automatically: i) activate the first array of multiple light sources, ii) measure a first light intensity with the first light energy sensors, iii) measure a second light intensity with the second light energy sensor, iv) compare the first light intensity to the second light intensity to determine an attenuation factor, v) apply the attenuation factor to the first light intensity to determine a time to achieve the target light dose, vi) adjust the time to achieve the target light dose based on the first light intensity and attenuation factor, and vii) deactivate the first array of multiple light sources after the time to achieve the target light dose has elapsed.

2. The device of claim 1 wherein the programmable controller is further configured to continuously measure the first light intensity, apply the attenuation factor and integrate over time to account for variations in the first light intensity, and adjust the time to achieve the target light dose accordingly.

3. The device of claim 1 wherein the first light energy sensors comprise photodiodes.

4. The device of claim 1 wherein the second light energy sensor comprises a UV-A sensor.

5. The device of claim 1 further comprising a second array of multiple light sources mounted in the housing on the second side of the tray and wherein the second light energy sensor comprises a photodiode associated with each of the multiple light sources in the second array.

* * * * *